United States Patent
Fortin et al.

(10) Patent No.: US 9,943,319 B2
(45) Date of Patent: *Apr. 17, 2018

(54) GRATER AND TRIAL LINER

(71) Applicant: DEPUY IRELAND UNLIMITED COMPANY, County Cork (IE)

(72) Inventors: Michael Fortin, Achushnet, MA (US); Larry McCleary, Warsaw, IN (US); Ken Hayes, Fall River, MA (US)

(73) Assignee: DEPUY IRELAND UNLIMITED COMPANY (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,188

(22) Filed: May 9, 2017

(65) Prior Publication Data
US 2017/0238942 A1    Aug. 24, 2017

Related U.S. Application Data

(63) Continuation of application No. 14/501,708, filed on Sep. 30, 2014, now Pat. No. 9,675,364.

(51) Int. Cl.
*A61B 17/16* (2006.01)
*A61F 2/46* (2006.01)

(52) U.S. Cl.
CPC ...... *A61B 17/1666* (2013.01); *A61B 17/1617* (2013.01); *A61F 2/4684* (2013.01)

(58) Field of Classification Search
CPC . A61B 17/16; A61B 17/1615; A61B 17/1617; A61B 17/1662; A61B 17/1664; A61B 17/1666; A61B 17/1684; A61F 2/46; A61F 2/4603; A61F 2/4609; A61F 2/4684

USPC .......................................................... 606/81
See application file for complete search history.

(56) References Cited

U.S. PATENT DOCUMENTS

| | | | | |
|---|---|---|---|---|
| 4,023,572 A | * | 5/1977 | Weigand | A61B 17/1666 30/276 |
| 4,712,951 A | * | 12/1987 | Brown | A61B 17/1666 408/158 |
| 4,802,468 A | * | 2/1989 | Powlan | A61B 17/1666 606/81 |
| 5,295,992 A | | 3/1994 | Cameron | |
| 5,431,657 A | * | 7/1995 | Rohr | A61F 2/4609 606/91 |

(Continued)

FOREIGN PATENT DOCUMENTS

| | | |
|---|---|---|
| DE | 2437772 A1 | 2/1976 |
| JP | 2006288863 A | 10/2006 |
| WO | WO 2007121313 A2 | 10/2007 |

*Primary Examiner* — Eric S Gibson

(57) ABSTRACT

An instrument for preparing an acetabulum. The instrument includes a handle having a reamer coupling feature and a trial coupling feature. The instrument further includes an acetabular reamer having an outer cutting surface and an inner concave surface having an apex. The acetabular reamer has a first handle coupling feature located at the apex adapted to couple to the reamer coupling feature of the handle. A trial having an outer convex surface having an apex is also included. The outer convex surface adapted to fit inside the inner concave surface of the acetabular reamer. The trial has a second handle coupling feature located at the apex of the outer convex surface adapted to couple to the trial coupling feature of the handle.

18 Claims, 7 Drawing Sheets

(56) References Cited

U.S. PATENT DOCUMENTS

| | | | | |
|---|---|---|---|---|
| 5,462,548 A * | 10/1995 | Pappas | A61B 17/1666 | 606/80 |
| 5,540,697 A * | 7/1996 | Rehmann | A61F 2/4609 | 294/95 |
| 5,584,837 A * | 12/1996 | Petersen | A61F 2/4609 | 606/86 R |
| 5,879,355 A * | 3/1999 | Ullmark | A61B 17/885 | 606/92 |
| 5,976,148 A * | 11/1999 | Charpenet | A61F 2/34 | 606/100 |
| 6,015,411 A | 1/2000 | Ohkoshi | | |
| 6,102,915 A | 8/2000 | Bresler | | |
| 6,168,600 B1 * | 1/2001 | Grace | A61B 17/1666 | 606/81 |
| 6,221,076 B1 * | 4/2001 | Albrektsson | A61B 17/1666 | 407/54 |
| 6,409,732 B1 | 6/2002 | Salyer | | |
| 6,875,217 B2 * | 4/2005 | Wolford | A61B 17/1617 | 606/81 |
| 7,220,264 B1 * | 5/2007 | Hershberger | A61B 17/1666 | 606/81 |
| 7,335,207 B1 * | 2/2008 | Smith | A61F 2/4609 | 606/80 |
| 7,621,921 B2 * | 11/2009 | Parker | A61F 2/34 | 606/91 |
| 7,744,602 B2 * | 6/2010 | Teeny | A61F 2/4609 | 606/100 |
| 7,763,031 B2 * | 7/2010 | Tulkis | A61B 17/1666 | 606/81 |
| 8,123,815 B2 * | 2/2012 | Meridew | A61F 2/34 | 623/22.29 |
| 8,308,810 B2 * | 11/2012 | Meridew | A61F 2/34 | 623/22.19 |
| 8,357,163 B2 * | 1/2013 | Sidebotham | A61B 17/1617 | 606/80 |
| 8,435,243 B2 * | 5/2013 | White | A61B 17/1666 | 606/79 |
| 8,556,897 B2 * | 10/2013 | Sidebotham | A61B 17/1617 | 606/81 |
| 8,771,275 B2 * | 7/2014 | Xie | A61B 17/1666 | 606/81 |
| 8,870,886 B2 * | 10/2014 | Burgi | A61B 17/56 | 606/91 |
| 9,439,781 B2 * | 9/2016 | Gibson | A61F 2/4609 | |
| 2003/0050645 A1 * | 3/2003 | Parker | A61F 2/4609 | 606/99 |
| 2003/0130741 A1 * | 7/2003 | McMinn | A61B 17/1617 | 623/23.14 |
| 2004/0073224 A1 * | 4/2004 | Bauer | A61B 17/1666 | 606/81 |
| 2004/0073226 A1 * | 4/2004 | Cotting | A61F 2/34 | 606/91 |
| 2004/0117029 A1 * | 6/2004 | Lewis | A61F 2/4684 | 623/22.28 |
| 2004/0133210 A1 | 7/2004 | Wolford | | |
| 2005/0038443 A1 * | 2/2005 | Hedley | A61B 17/162 | 606/91 |
| 2005/0085823 A1 * | 4/2005 | Murphy | A61F 2/34 | 606/91 |
| 2005/0228394 A1 * | 10/2005 | Bihary | A61F 2/4609 | 606/91 |
| 2005/0261694 A1 * | 11/2005 | Orton | A61B 17/1666 | 606/81 |
| 2006/0025774 A1 | 2/2006 | Fishbein | | |
| 2006/0079906 A1 * | 4/2006 | Timperley | A61B 17/1666 | 606/81 |
| 2007/0203583 A1 * | 8/2007 | Slone | A61B 17/1666 | 623/22.28 |
| 2007/0233132 A1 * | 10/2007 | Valla | A61B 17/1666 | 606/81 |
| 2007/0276394 A1 * | 11/2007 | Johnson | A61B 17/1666 | 606/80 |
| 2008/0009952 A1 * | 1/2008 | Hodge | A61B 17/1666 | 623/22.21 |
| 2009/0088757 A1 | 4/2009 | Tulkis | | |
| 2009/0163921 A1 | 6/2009 | Lechot | | |
| 2010/0069908 A1 * | 3/2010 | Sidebotham | A61B 17/1617 | 606/81 |
| 2010/0168749 A1 * | 7/2010 | Sidebotham | A61B 17/1617 | 606/79 |
| 2010/0272533 A1 | 10/2010 | Hecht | | |
| 2011/0208202 A1 * | 8/2011 | Zumsteg | A61F 2/4609 | 606/91 |
| 2011/0213372 A1 * | 9/2011 | Keefer | A61B 17/1659 | 606/85 |
| 2012/0185059 A1 * | 7/2012 | Vankoski | A61F 2/4684 | 623/22.24 |
| 2013/0131741 A1 * | 5/2013 | Kourtis | A61F 2/4603 | 606/86 R |
| 2013/0211407 A1 * | 8/2013 | Geebelen | A61B 17/1631 | 606/80 |
| 2013/0325139 A1 * | 12/2013 | Steiner | A61F 2/4684 | 623/22.15 |
| 2014/0114321 A1 * | 4/2014 | Davenport | A61F 2/4609 | 606/91 |
| 2014/0163564 A1 * | 6/2014 | Bollinger | A61B 17/1666 | 606/91 |
| 2014/0228854 A1 * | 8/2014 | Witt | A61B 17/1746 | 606/96 |
| 2014/0324183 A1 * | 10/2014 | Springer | A61F 2/4609 | 623/22.24 |
| 2015/0100060 A1 * | 4/2015 | Black | A61F 2/4609 | 606/91 |
| 2015/0366568 A1 * | 12/2015 | Victor | A61B 17/1615 | 606/81 |
| 2016/0089156 A1 * | 3/2016 | Fortin | A61B 17/1666 | 606/81 |
| 2016/0089158 A1 * | 3/2016 | Fortin | A61B 17/1666 | 606/81 |
| 2016/0175112 A1 * | 6/2016 | Pruvost | A61F 2/4609 | 606/81 |

* cited by examiner

GRATER AND TRIAL LINER

CROSS REFERENCE TO RELATED APPLICATION

This application is a continuation of U.S. patent application Ser. No. 14/501,708, filed Sep. 30, 2014.

TECHNICAL FIELD OF THE INVENTION

The present invention relates generally to the field of orthopedics, and, more particularly, to an instrument for reaming an acetabulum.

BACKGROUND

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the ankle permits a hinge movement, the knee allows for a combination of gliding and hinge movements and the shoulder and hip permit movement through a ball and socket arrangement.

The joints in the body are stressed or can be damaged in a variety of ways. Gradual wear and tear is imposed on the joints through the continuous use of a joint over the years. The joints that permit motion have cartilage positioned between the bones providing lubrication to the motion and also absorbing some of the forces direct for the joint. Over time, the normal use of a joint may wear down the cartilage and bring the moving bones in a direct contact with each other. In contrast, in normal use, a trauma to a joint, such as the delivery of a large force from an automobile accident for example, may cause considerable damage to the bones, the cartilage or to other connective tissue such as tendons or ligaments.

Arthropathy, a term referring to a disease of the joint, is another way in which a joint may become damaged. One form of joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthropathy is osteonecrosis, which is caused by the death of a part of the bone due to loss of blood supply and subsequent degeneration of the cartilage. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted. The hip joint is a ball and socket joint that joins the femur or thighbone with the pelvis. The pelvis has a hemispherical socket called the acetabulum for receiving the head of the femur. Both the head of the femur and the acetabulum are coated with cartilage for allowing the femur to articulate within the pelvis. Other joints commonly afflicted include those of the spine, knee, shoulder, elbow, carpals, metacarpals, and phalanges of the hand. One means to address this affliction is arthroplasty which commonly refers to the making of an artificial joint. In severe cases of arthritis or other forms of arthropathy, such as when pain is overwhelming or when a joint has a limited range of mobility, a partial or total replacement of the joint may be justified. The procedure for replacing the joint varies, of course, with the particular joint in question, but in general involves replacing a terminal portion of an afflicted bone with a prosthetic implant and inserting a member with structural support to serve as a substitute for the cartilage.

The prosthetic implant is formed of a rigid material that becomes bonded with the bone and provides strength and rigidity to the joint and a bearing member chosen to allow for lubrication to the joint. Suitable materials for the implant include metals and composite materials such as titanium, cobalt chromium, stainless steel, ceramic and suitable materials for the bearing include polyethylene, metal and ceramics. A cement may also be used to secure the prosthetic implant to the host bone.

Total hip replacement, for example, involves removing the ball shaped head of the femur and inserting a stemmed implant into the center of the bone, which is referred to as the medullary canal of the bone. The stem implant may be cemented into the medullary canal or may have a porous coated surface for allowing the bone to heal directly to the implant. The stemmed implant has a neck and a ball shaped head, which are intended to perform the same functions as the neck and head of a healthy femur. The acetabulum of the patient is reamed to receive a shell and liner. A polyethylene, metal, or ceramic liner with a metal shell is inserted into the acetabulum and acts as socket for receiving the head on the stemmed implant.

While performing the surgery, it would be beneficial to have a liner that can be trialed off of the acetabular reamer. Also, it would be helpful if the same tool could be used to insert both the trial and perform the reaming function.

SUMMARY OF THE INVENTION

According to one embodiment of the present invention, an instrument for preparing an acetabulum is provided. The instrument includes a handle having a reamer coupling feature and a trial coupling feature. The instrument further includes an acetabular reamer having an outer cutting surface and an inner concave surface having an apex. The acetabular reamer has a first handle coupling feature located at the apex adapted to couple to the reamer coupling feature of the handle. A trial having an outer convex surface having an apex is also included. The outer convex surface adapted to fit inside the inner concave surface of the acetabular reamer. The trial has a second handle coupling feature located at the apex of the outer convex surface adapted to couple to the trial coupling feature of the handle.

According to another embodiment of the present invention, a method for preparing and trialing an acetabulum is provided. The method includes coupling a handle to an acetabular reamer. The acetabular reamer has an outer cutting surface and an inner concave surface having an apex. Next, the user reams the acetabulum to a desired depth and uncouples the handle from the acetabular reamer. The user couples the handle to a trial, the trial having an outer convex surface having an apex and then inserts the trial into the acetabular reamer. The outer convex surface of the trial is adapted to fit into the inner concave surface of the acetabular reamer.

According to yet another embodiment of the present application, an instrument for preparing an acetabulum is provided. The instrument includes a handle having a hexshaped rod and a sleeve having a recess extending around and outer periphery of the sleeve. The instrument further includes an acetabular reamer having an outer cutting surface and an inner concave surface having an apex. The acetabular reamer has a recess located at the apex adapted to couple to the hex-shaped rod of the handle. A trial having an outer convex surface having an apex is also included. The outer convex surface is adapted to fit inside the inner concave surface of the acetabular reamer. The trial has a plurality of flexible fingers located at the apex of the outer convex surface adapted to engage to the recess on the sleeve of the handle.

DETAILED DESCRIPTION

Figure 1:
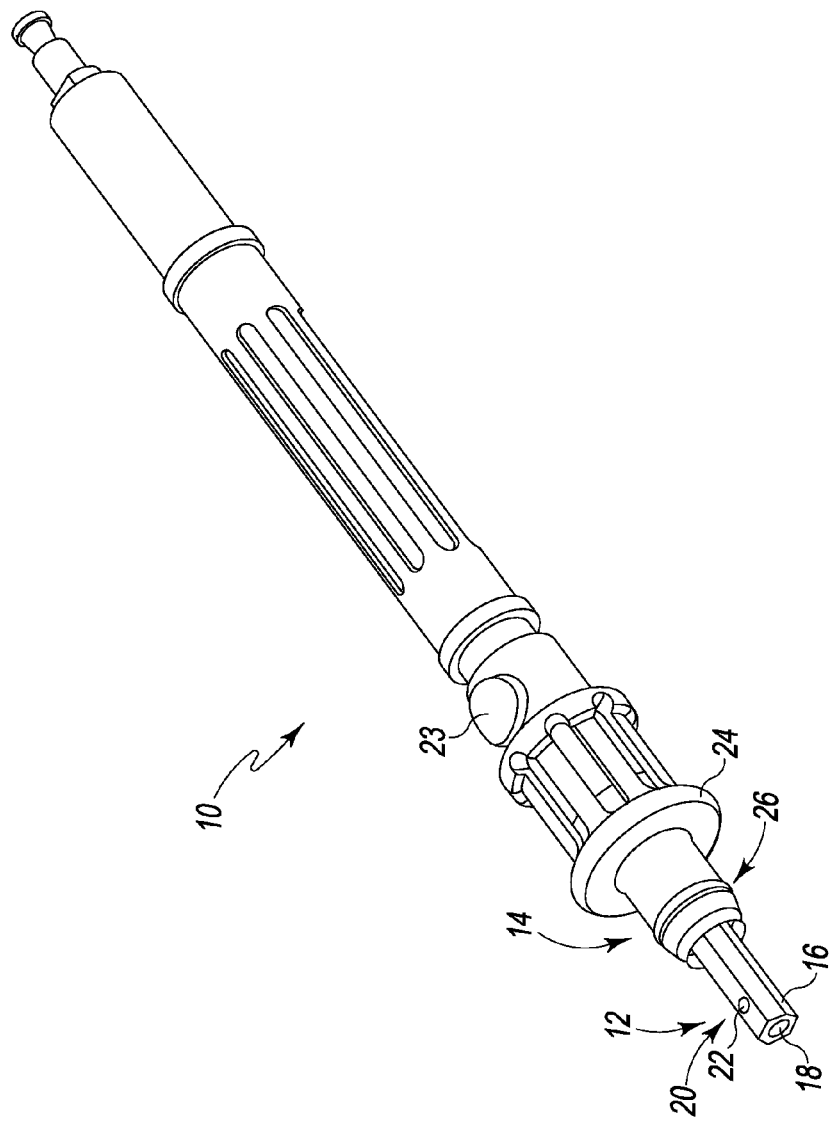
FIG. 1 is a perspective view of a handle of an instrument according to one embodiment of the present invention.

Like reference numerals refer to like parts throughout the following description and the accompanying drawings. Turning now to FIG. 1, a handle 10 of an instrument 11 (FIG. 4) according to one embodiment of the present invention is illustrated. The handle 10 includes a reamer coupling feature 12 and a trial coupling feature 14. The reamer coupling feature 12 includes a hex-shaped rod 16 having a hex-shaped end 18. Whilst the reamer coupling feature 12 is illustrated as a hex-shaped rod, it is understood other types of coupling mechanisms may be used such as rods with buttons or latches. The hex-shaped rod 16 may also include a locking mechanism 20. The locking mechanism in this embodiment is illustrated as a pair of ball bearings 22 that protrude from the rod 16. The ball bearings 22 are coupled to a button 23, such that as the button 23 is pressed, the ball bearings retract. Other locking mechanisms such as latches or buttons may be used.

The trial coupling feature 14 is illustrated as a slidable sleeve 24 having a recess 26 at one end. The sleeve 24 may be of any configuration which allows it slide along the handle 10.

Figure 2:
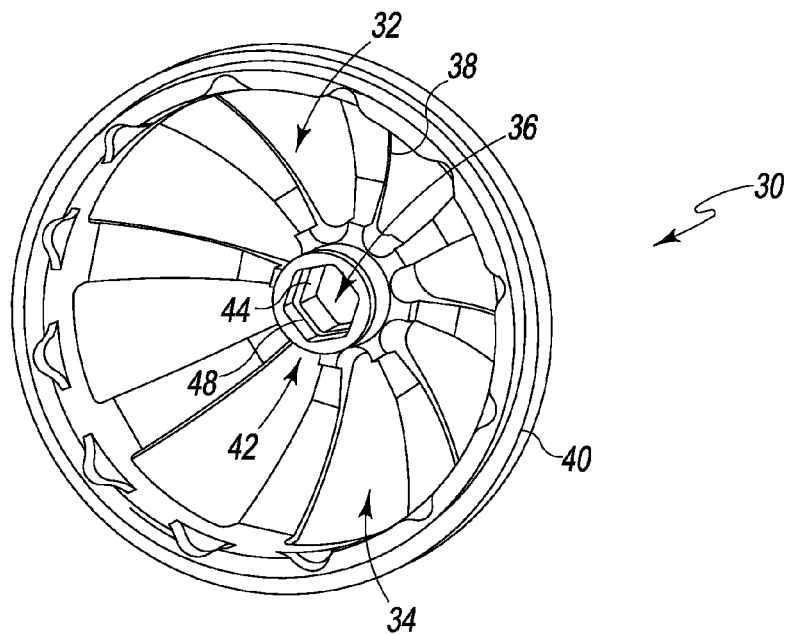
FIG. 2 is an inside view of a reamer to be coupled to the handle of FIG. 1.

Turning now to FIG. 2, an inside view of an acetabular reamer 30 is shown. The acetabular reamer 30 includes an outer cutting surface 32 and an inner concave surface 34. The acetabular reamer 30 includes an apex 36. The outer cutting surface 32 may include a plurality of cutting blades 38 extending from the apex 36 to a rim 40 opposite the apex 36.

Figure 4:
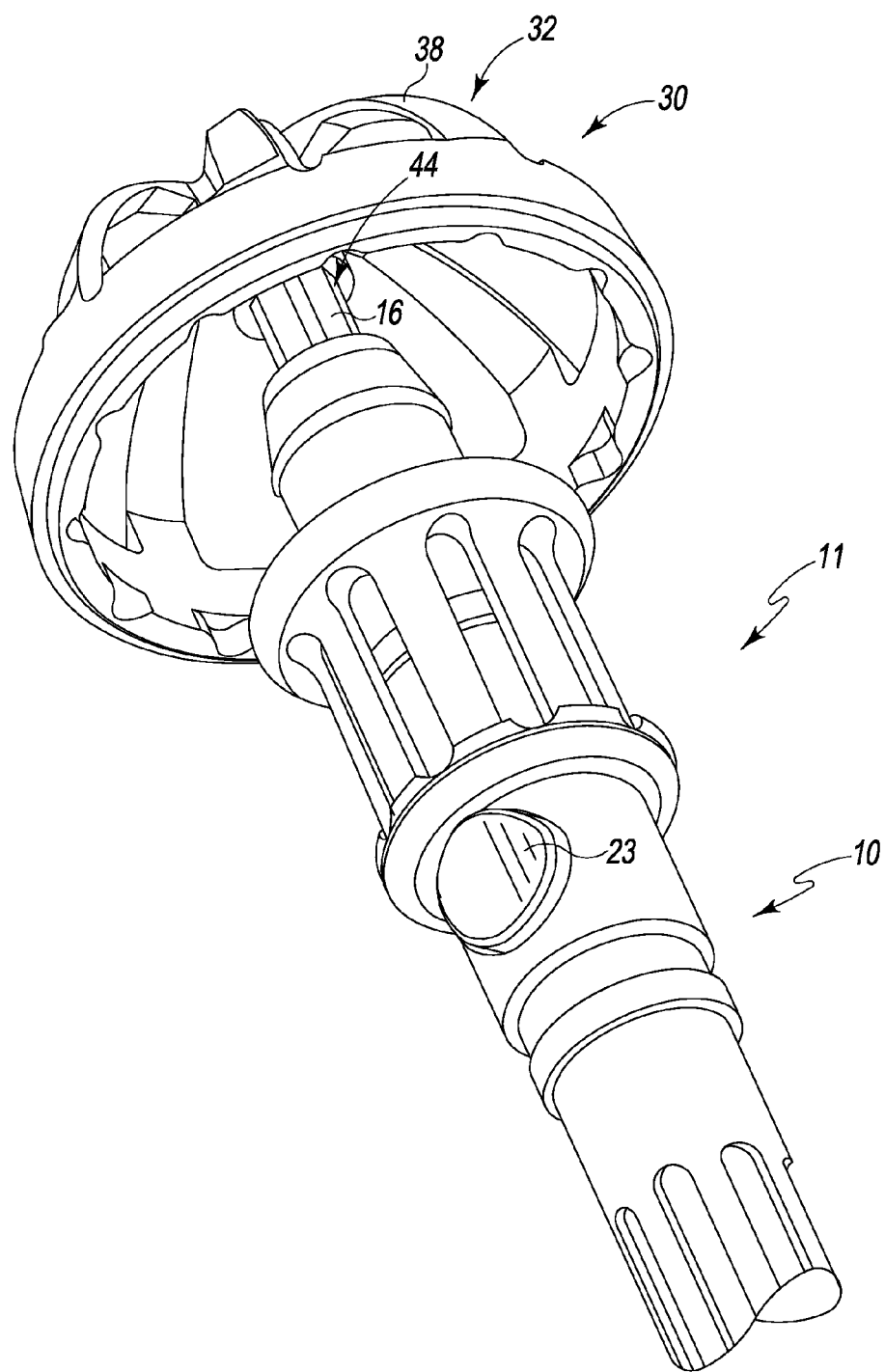
FIG. 4 is a perspective view of the handle of FIG. 1 coupled to the reamer of FIG. 2.

The inner concave surface 34 includes a first handle coupling feature 42 at the apex 36. The first handle coupling feature 42 may be a female hex boss 44. The female hex boss 44 is sized and shaped to engage the hex-shaped rod 16 of the handle 10. When coupled (as indicated in FIG. 4), the hex shaped rod 16 engages the female hex boss 44 such that when the rod 16 is rotated, the rod engages the boss causing the boss and thus the reamer 30 to rotate. The female hex boss 44 may also include a recess (or locking feature) 48 extending around its inner periphery. The recess 48 may be used in conjunction with a trial 60 as detailed further below. Although a female hex boss 44 is illustrated as the first handle coupling feature, other coupling devices known by those skilled in the art may be used. Also, the locking feature 48 may be of locking mechanisms other than a recess.

Figure 3:
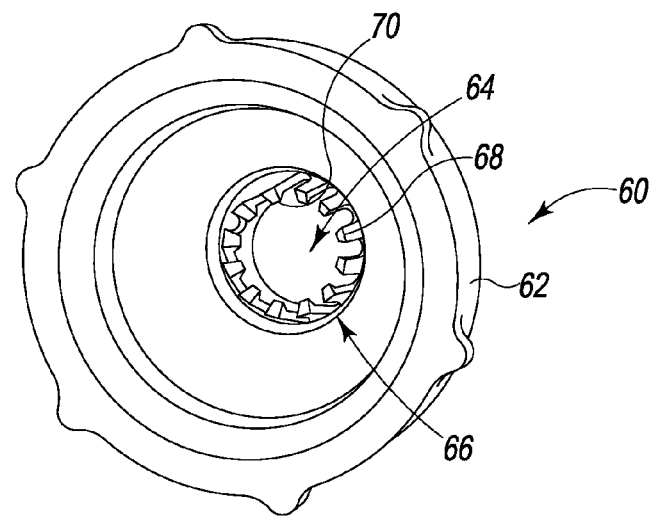
FIG. 3 is an inside view of a trial to be coupled with the handle of FIG. 1.

Turning now to FIG. 3, a trial 60 according to one embodiment of the present invention is illustrated. The trial 60 includes a convex outer surface 62 and an apex 64. The convex outer surface 62 is designed to fit inside the inner concave surface 34 of the reamer 30. At the apex 64, the trial 60 includes a second handle coupling feature 66. In this embodiment, the second handle coupling feature 66 is a plurality of flexible fingers 68 which extend from the apex 64 and into a recess of the trial 60. The flexible fingers 68 include a protrusion 70. The protrusion 70 is adapted to grasp the recess 26 of the sleeve 24 when the trial is coupled to the handle 10.

FIG. 4 illustrates an embodiment of the instrument 11 with the handle 10 coupled with the acetabular reamer 30. As shown, the hex-shaped rod 16 of the handle 10 fits into the female hex boss 40 of the reamer 30. In use, as the handle 10 is rotated, the edges of the hex-shaped rod 16 will engage the edges of the female hex boss 40, causing the reamer 30 to also turn. The ball bearings 22 (FIG. 1) will engage recess 48 (FIG. 2) of the female hex boss 40 to lock the handle 10 to the reamer 30. Once the user is done reaming the acetabulum, the user may depress the button 23, which causes the ball bearings 22 to disengage the recess 48.

Figure 5:
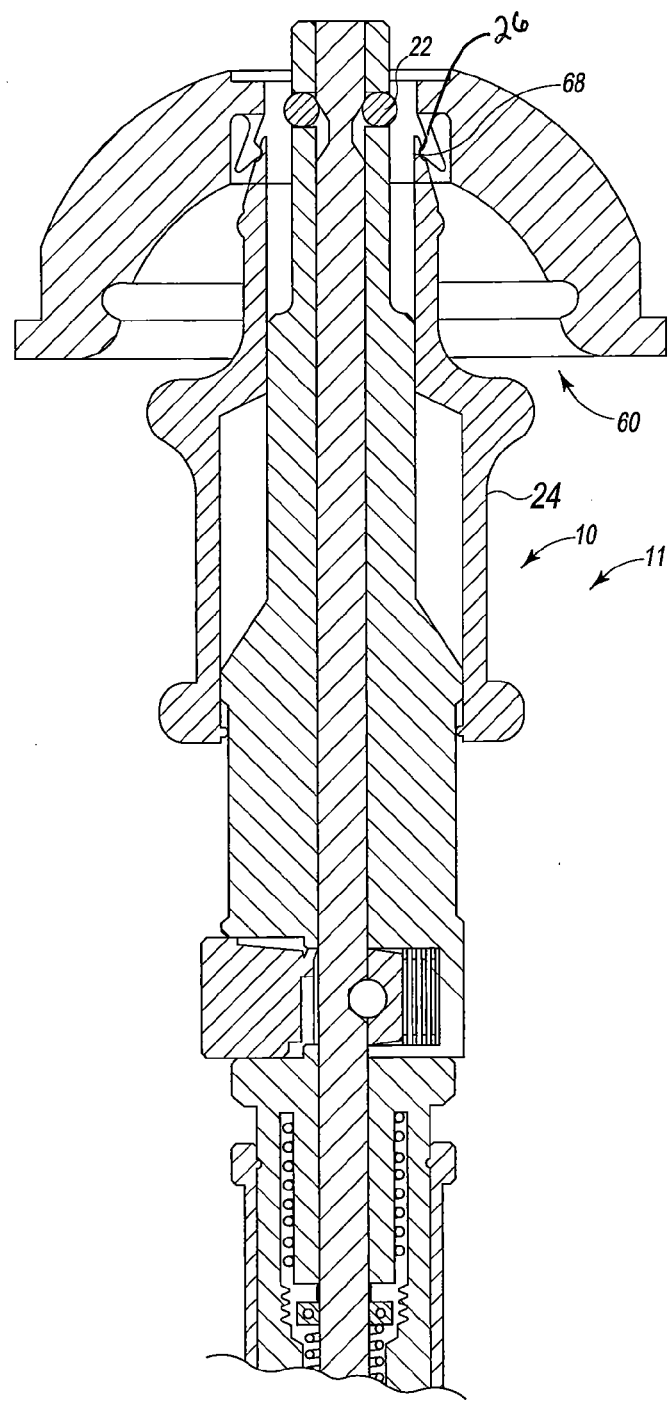
FIG. 5 is a cut-away view of the handle of FIG. 1 coupled to the trial of FIG. 3.

FIG. 5 is a cross-sectional view of the handle 10 coupled to the trial 60. As shown, the sleeve 24 of the handle 10 can be slid along the handle 10. When the sleeve 24 is slid to an end, the fingers 68 engage the recess 26 of the sleeve. This causes the trial 60 to be locked into place with respect to the handle 10. To disengage the trial 60 from the handle 10, the user slides the sleeve toward the other end of the handle 10. The flexible fingers 68 will flex and disengage from the trial.

Figure 6:
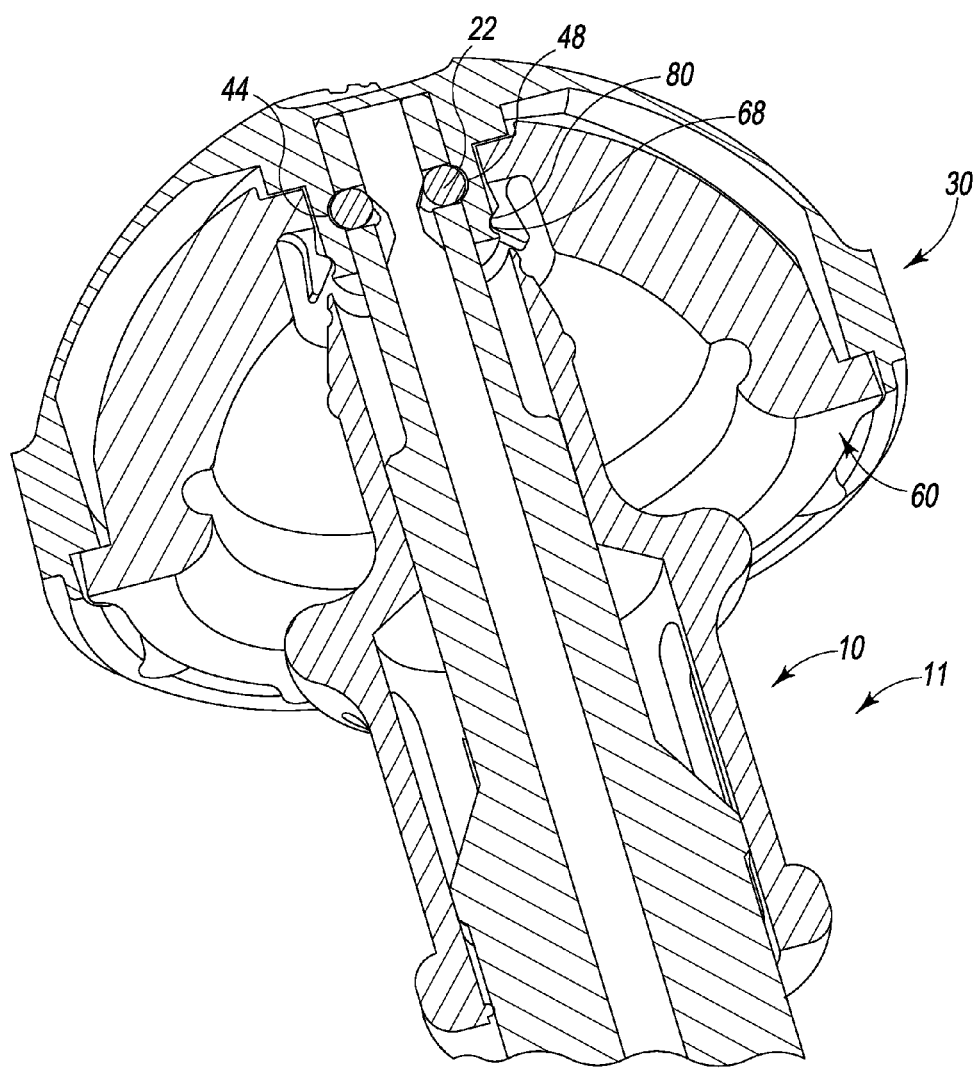
FIG. 6 is a cut-away view of the handle of FIG. 1 coupled to the trial of FIG. 3 and the reamer of FIG. 2.

FIG. 6 is a cross-sectional view of the handle 10, the trial 60 and the reamer 30. The view is of the handle 10 just after it has disengaged from the trial 60 and the trial 60 has engaged the reamer 30. As shown, the flexible fingers 68 of the trial 60 have been snap-fit into a recess 80 on the outside of the female hex boss 44. This view also shows the ball bearings 22 of the handle 10 engaged with the recess 48 of the hex boss 44. If the user continues to push the sleeve 24 into the trial 60, it causes the trial to disengage from the reamer 30 and the trial 60 would engage the sleeve 24, allowing the user to remove the trial 60 from the reamer 30.

Figure 7:
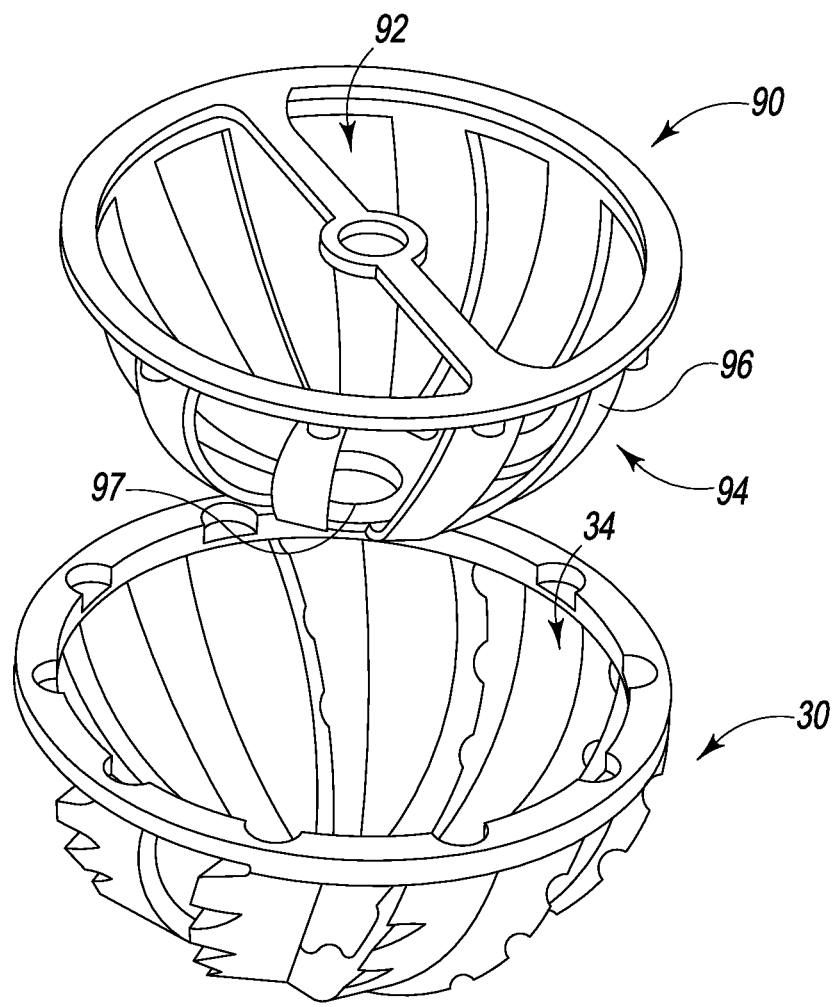
FIG. 7 is a perspective view of the reamer of FIG. 2 and a bone strainer according to one embodiment of the invention.

Turning now to FIG. 7, a bone strainer 90 according to one embodiment of the invention is illustrated. The bone strainer 90 is a generally hemispherical part having an inner concave cavity 92 and an outer convex shell 94 that is designed to fit inside the inner concave surface 34 of the reamer 30. The bone strainer 90 includes a plurality of curved arms 96 that extend from an apex 97 to a rim 98. The apex 97 engages the boss 44 (FIG. 2) of the reamer 30. During use, the plurality of curved pieces 96 act to retain the reamed bone chips during the reaming process. When the user is done reaming the acetabulum, the user can remove the bone strainer 90 and handle 10. The bone chips are removed with the bone strainer 90, leaving a clean surface in order to place the trial 60.

Figure 8:
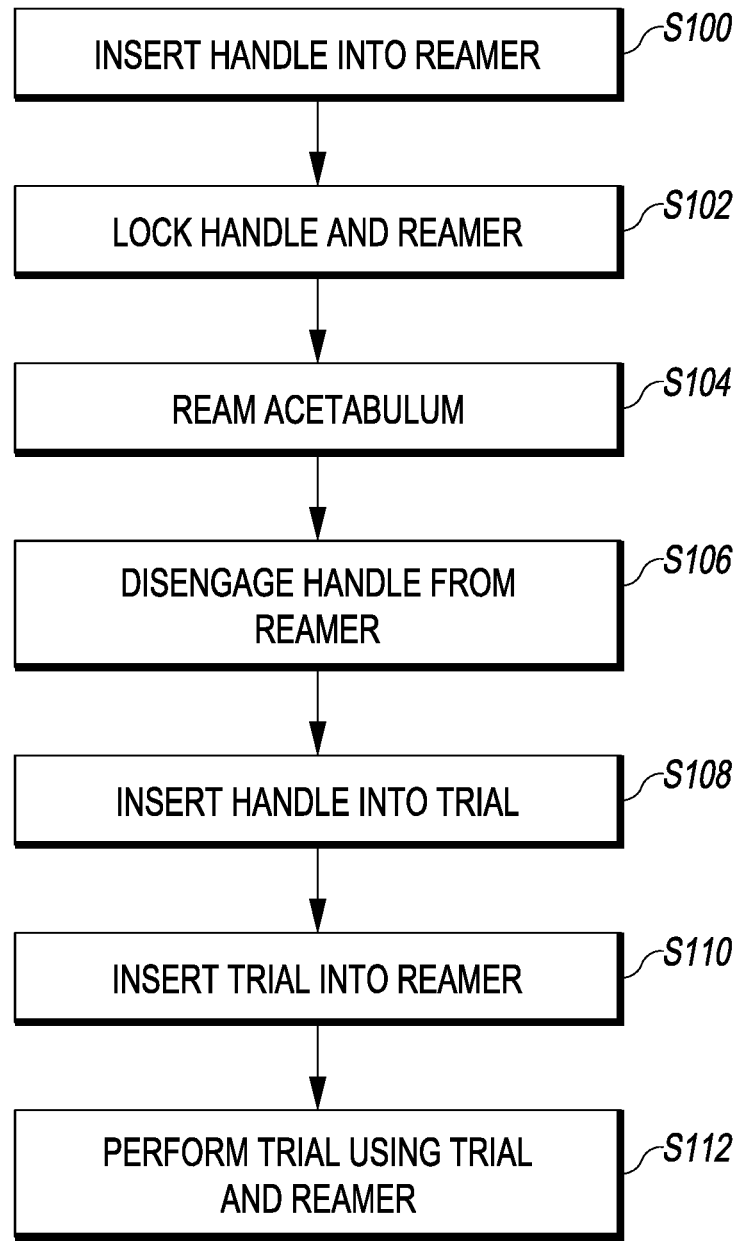
FIG. 8 is a flow chart illustrating the use of an instrument according to one embodiment of the present invention.

Turning now to FIG. 8, a flow chart describing the use of the instrument 11 is shown. First, at step s100, the handle 10 is inserted into the reamer 30 and the bone strainer 90, with the hex-shaped rod 16 engaging the female hex boss 44 of the reamer. The reamer 30 is then locked to the handle 10 via the ball bearings 22 engaging the recess 48 of the reamer 30 (step s102). The user reams the acetabulum by rotating the handle 10 at step s104. As described above, as the handle 10 is rotated, the edges of the hex-shaped rod 16 engage the edges of the female hex boss 44, causing the reamer 30 to also rotate. As the reamer 30 rotates, the cutting blades 38 on the outer cutting surface 32 ream the acetabular bone (step s104). During this step, as the bone is cut away, the bone strainer 90 collects the bone in its cavity 92.

After reaming, the handle 10 is disengaged from the reamer 30 at step s106 by pressing the button 23. The reamer 30 is left in the reamed acetabulum, while the handle 10 and bone strainer 90 are removed. The bone strainer 90 also removes the bone chips, thereby leaving a clean reamer to receive the trial 60. The handle 30 is then inserted into the trial 60 (step s108). As described above, the flexible fingers 68 of the trial snap-fit into the recess 26 of the handle 10. More specifically, the flexible fingers 68 include protrusions 70 that engage the recess 26. The handle is then removed. The trial 60 is then inserted into the reamer 30 (step s110). As the trial 60 is pushed into the reamer, the fingers 68 engage the recess 80 of the outside of the female hex boss 44. The trial 60 is now locked in position relative to the reamer and the trial reduction can be done (step s112).

The reamer, bone strainer, and handle may be made from a variety of known materials such as stainless steel. Other metals may also be used. In some embodiments, plastics may be used or a combination of plastic and metal. The trial 60 may be made of a plastic such as polyacetal. Other known materials such as polyethylenes or other plastic materials may be used. The trial may also be made of other materials such as ceramics or metals.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

The invention claimed is:

1. An instrument for preparing an acetabulum, the instrument comprising:
 a handle having a reamer coupling feature and a trial coupling feature;
an acetabular reamer having an outer cutting surface and an inner concave surface having an apex, the acetabular reamer having a first handle coupling feature located at the apex adapted to couple to the reamer coupling feature of the handle; and
 a trial having an outer convex surface having an apex, the outer convex surface adapted to fit inside the inner concave surface of the acetabular reamer, the trial having a second handle coupling feature located at the apex of the outer convex surface adapted to couple to the trial coupling feature of the handle;
 wherein the trial coupling feature includes a slidable sleeve having a locking recess and the second handle coupling feature having flexible fingers adapted to engage the locking recess of the slidable sleeve; and
 wherein the reamer coupling feature of the handle includes a locking feature and the first handle coupling feature of the reamer includes a locking feature, wherein the locking feature of the reamer coupling feature is adapted to engage the locking feature of the first handle coupling feature.

2. The instrument of claim 1, wherein the reamer coupling feature of the handle is a rod having a hex-shaped end and the first handle coupling feature is a hex-shaped boss located in the apex of the reamer.

3. The instrument of claim 1, wherein the first handle coupling feature includes an outer periphery having a recess and the flexible fingers of the second handle coupling feature are adapted to engage the recess of the outer periphery.

4. The instrument of claim 1, wherein the locking feature of the reamer coupling feature is a pair of moveable balls and the locking feature of the first handle coupling feature is a recess.

5. The instrument of claim 4, wherein the handle further includes a button, the button coupled to the moveable balls, such that when the button is activated the balls retract, releasing the handle from the reamer.

6. The instrument of claim 1, further comprising a bone chip clearer, the bone chip clearer having a convex outer surface with an apex, the convex outer surface adapted to engage the concave inner surface of the reamer, and the apex of the bone chip clearer having a recess adapted to receive the reamer coupling feature of the handle.

7. A method for preparing and trialing an acetabulum comprising:
 coupling a handle to an acetabular reamer, the acetabular reamer having an outer cutting surface and an inner concave surface having an apex;
reaming the acetabulum to a desired depth;
 uncoupling the handle from the acetabular reamer;
 coupling the handle to a trial, the trial having an outer convex surface having an apex; and
 inserting the trial into the acetabular reamer, wherein the outer convex surface of the trial is adapted to fit into the inner concave surface of the acetabular reamer; wherein a trial coupling feature includes a slidable sleeve having a locking recess and a second handle coupling feature having flexible fingers adapted to engage the locking recess of the slidable sleeve.

8. The method of claim 7, wherein the coupling of the handle to the acetabular reamer includes using a hex-shaped rod on the handle to couple to a hex-shaped recess on the reamer.

9. The method of claim 7, further comprising locking the handle to the acetabular reamer.

10. The method of claim 9, wherein the locking comprises engaging ball bearings on the handle into a recess on the acetabular reamer.

11. The method of claim 7, further comprising coupling the trial to the acetabular reamer to perform a trial reduction of the hip joint.

12. The method of claim 7, further comprising coupling a handle to a bone chip collector, the bone chip collector having an outer convex surface adapted to fit within the inner concave surface of the acetabular reamer.

13. An instrument for preparing an acetabulum, the instrument comprising:
 a handle having a hex-shaped rod and a sleeve having a recess extending around and outer periphery of the sleeve;
 an acetabular reamer having an outer cutting surface and an inner concave surface having an apex, the acetabular reamer having a recess located at the apex adapted to couple to the hex-shaped rod of the handle; and
 a trial having an outer convex surface having an apex, the outer convex surface adapted to fit inside the inner concave surface of the acetabular reamer, the trial having a plurality of flexible fingers located at the apex of the outer convex surface adapted to engage to the recess on the sleeve of the handle;

wherein a trial coupling feature includes a slidable sleeve having a locking recess.

14. The instrument of claim 13, wherein the reamer includes a plurality of anti-rotation recesses and the trial includes a plurality of anti-rotation protrusions adapted to engage the anti-rotation recesses of the reamer.

15. The instrument of claim 14, wherein the handle further includes a release adapted to release the locking mechanism of the handle.

16. The instrument of claim 13, wherein the handle further includes a locking mechanism adapted to lock the handle to the reamer during use.

17. The instrument of claim 13, further comprising a bone strainer having an outer convex shell and inner concave cavity, wherein an apex of the bone strainer is adapted to engage the reamer.

18. The instrument of claim 17, wherein the outer convex shell is created by a plurality of spaced apart arms extending from the apex to a rim.

\* \* \* \* \*